(12) United States Patent
Duan et al.

(10) Patent No.: US 11,571,116 B2
(45) Date of Patent: Feb. 7, 2023

(54) CONTROL SYSTEM FOR CAPSULE ENDOSCOPE

(71) Applicant: Ankon Medical Technologies (Shanghai) Co., LTD., Shanghai (CN)

(72) Inventors: Xiaodong Duan, Pleasanton, CA (US); Shaobang Zhang, Shanghai (CN)

(73) Assignee: Ankon Medical Technologies (Shanghai) Co., LTD, Shanghai (CN)

(*) Notice: Subject to any disclaimer, the term of this patent is extended or adjusted under 35 U.S.C. 154(b) by 859 days.

(21) Appl. No.: 16/428,952

(22) Filed: May 31, 2019

(65) Prior Publication Data
US 2019/0365211 A1 Dec. 5, 2019

Related U.S. Application Data

(63) Continuation of application No. PCT/CN2019/089669, filed on May 31, 2019.

(60) Provisional application No. 62/679,791, filed on Jun. 2, 2018.

(51) Int. Cl.
*A61B 1/00* (2006.01)
*A61B 1/04* (2006.01)
*A61B 90/50* (2016.01)
*A61B 34/30* (2016.01)
*A61B 34/00* (2016.01)

(52) U.S. Cl.
CPC .......... *A61B 1/041* (2013.01); *A61B 1/00158* (2013.01); *A61B 34/30* (2016.02); *A61B 90/50* (2016.02); *A61B 1/00002* (2013.01); *A61B 34/73* (2016.02)

(58) Field of Classification Search
CPC . A61B 1/041; A61B 1/00158; A61B 1/00002; A61B 34/30; A61B 34/73; A61B 90/50
See application file for complete search history.

(56) References Cited

U.S. PATENT DOCUMENTS

| 5,810,712 | A | 9/1998 | Dunn | |
| 6,723,106 | B1* | 4/2004 | Charles | B25J 9/1065 |
| | | | | 606/130 |
| 10,485,409 | B2* | 11/2019 | Di Natali | A61B 1/041 |
| 2003/0191455 | A1 | 10/2003 | Sanchez | |

(Continued)

FOREIGN PATENT DOCUMENTS

| CN | 101001563 | 7/2007 |
| CN | 103419189 | 5/2012 |

(Continued)

*Primary Examiner* — Timothy J Neal
*Assistant Examiner* — William B Chou
(74) *Attorney, Agent, or Firm* — Treasure IP Group, LLC

(57) ABSTRACT

A control system for a capsule endoscope is provided. The control system includes a balance arm device, a mechanical arm, a permanent magnet and a 2-DOF rotary platform. The bottom of the balance arm device is fixed, and the active end of the balance arm device connects with a boom. The bottom of the mechanical arm is fixed, and the active end of the mechanical arm connects with a spherical hinge. The 2-DOF rotary platform is fixed below the boom and the permanent magnet is located in the 2-DOF rotary platform. The spherical hinge connects to the boom, assisting the permanent magnet to move around a fan-shaped area around a subject.

27 Claims, 15 Drawing Sheets

(56) References Cited

U.S. PATENT DOCUMENTS

| | | | |
|---|---|---|---|
| 2007/0191671 A1* | 8/2007 | Kawano | A61B 5/702 600/12 |
| 2011/0184235 A1* | 7/2011 | Schostek | A61B 1/00158 600/109 |
| 2013/0110128 A1 | 5/2013 | Schostek et al. | |
| 2014/0288416 A1* | 9/2014 | Mahoney | A61B 1/00158 600/118 |
| 2015/0018614 A1* | 1/2015 | Duan | A61B 1/041 600/109 |
| 2018/0353055 A1* | 12/2018 | Geiger | B25J 17/00 |
| 2019/0104994 A1* | 4/2019 | Valdastri | A61B 1/00158 |
| 2020/0138530 A1* | 5/2020 | Nowatschin | B25J 9/107 |

FOREIGN PATENT DOCUMENTS

| | | |
|---|---|---|
| CN | 103222842 | 7/2013 |
| CN | 203244366 | 10/2013 |
| CN | 203634116 | 6/2014 |

* cited by examiner

CONTROL SYSTEM FOR CAPSULE ENDOSCOPE

CROSS REFERENCE TO RELATED APPLICATIONS

The present invention takes priority of a U.S. provisional application 62/679,791 filed on Jun. 2, 2018. The disclosure is included in this application in its entirety.

FIELD OF INVENTION

The invention generally relates to a medical device, particularly refers to a control system for a capsule endoscope.

BACKGROUND

Capsule endoscope is a capsule-shaped medical device designed to examine human gastrointestinal tract. Generally, after the capsule endoscope is swallowed by the patient into their body, an external magnetic control device guides the device to move in the GI tract, so as to view the health status of the gastrointestinal and esophageal regions of the patient and help the doctor to make a diagnosis.

A control system for the capsule endoscope of prior art comprises a capsule endoscope for collecting information of the digestive tract of the patient to be examined, wherein a permanent magnet is provided; a capsule endoscope control device for controlling the movement of the capsule endoscope by the permanent magnet; a control terminal for receiving and displaying digestive tract information and capsule endoscope position information as well as controlling the operation of the capsule endoscope control device. After moving to a first position to be examined under control of the capsule endoscope control device, the capsule endoscope can send information of the digestive tract at the first position to the control terminal and display, so that the examiner can clearly observe the digestive tract conditions of the patient. Then, move the capsule endoscope to a second position for examination, and send the digestive tract conditions to the control terminal. Therefore, all target positions can be examined by this way.

The robot of the control system for the capsule endoscope is fixed on a control cabinet with casters and can move around with the movement of the control cabinet. However, this kind of movement may cause the robot to crash into the surrounding examination bed or control terminal, affecting the patient experience, or even damaging the precision instrument.

In addition, an active magnet is suspended below the robot arm of the control system. As the robot arm reaches a designated position, the active magnet is controlled to move and exert an magnetic attraction force on the permanent magnet in the capsule endoscope, and thereby drive the capsule endoscope to move in the digestive tract. However, since the active magnet under the robot arm is heavy, vertical movement needs to overcome the effect of gravity. As a precision machine, the robot arm provides limited loading capacity and is costly. Long-time heavy load may cause the robot arm to be deformed and even damaged, affecting the examination accuracy consequently.

Further, in the above solution, the control of the capsule by the control system is transmitted through human-control terminal—computer-server-motor-permanent magnet, so that the overall system structure is complicated and the operation is inconvenient. In addition, the examination position is fixed, so all-round scanning and control are impossible.

Moreover, the control system can be a mechanical arm for controlling an active magnet connected to the mechanical arm, and achieve the purpose for controlling the capsule endoscope. At this time, the active magnet is too heavy that can result in heavy bearings and high costs of motors of the mechanical arm.

Therefore, it is necessary to provide a control system for the capsule endoscope that features simplified structure, easy operation, low cost and provides all-round scanning and control capability.

SUMMARY OF THE INVENTION

The present invention discloses a control system for a capsule endoscope, comprising a balance arm device, a mechanical arm, a permanent magnet and a 2-DOF rotary platform; wherein the bottom of the balance arm device is fixed, and the active end of the balance arm device connects with a boom; wherein the bottom of the mechanical arm is fixed, and the active end of the mechanical arm connects with a spherical hinge; wherein the 2-DOF rotary platform is fixed below the boom and the permanent magnet is located in the 2-DOF rotary platform; wherein the spherical hinge connects to the boom, assisting the permanent magnet to move around an area around a subject.

It is one object of the present invention that the balance arm device is a pneumatic balance arm or a spring assisted balance arm.

It is another object of the present invention that the balance arm device and the mechanical arm are fixed to different fixing objects or a same fixing object.

It is another object of the present invention that the control system uses the balance arm device in conjunction with the mechanical arm to provide a 5-DOF movement range, and realize free control of a capsule endoscope through control of the permanent magnet.

DETAILED DESCRIPTION

Figure 1:
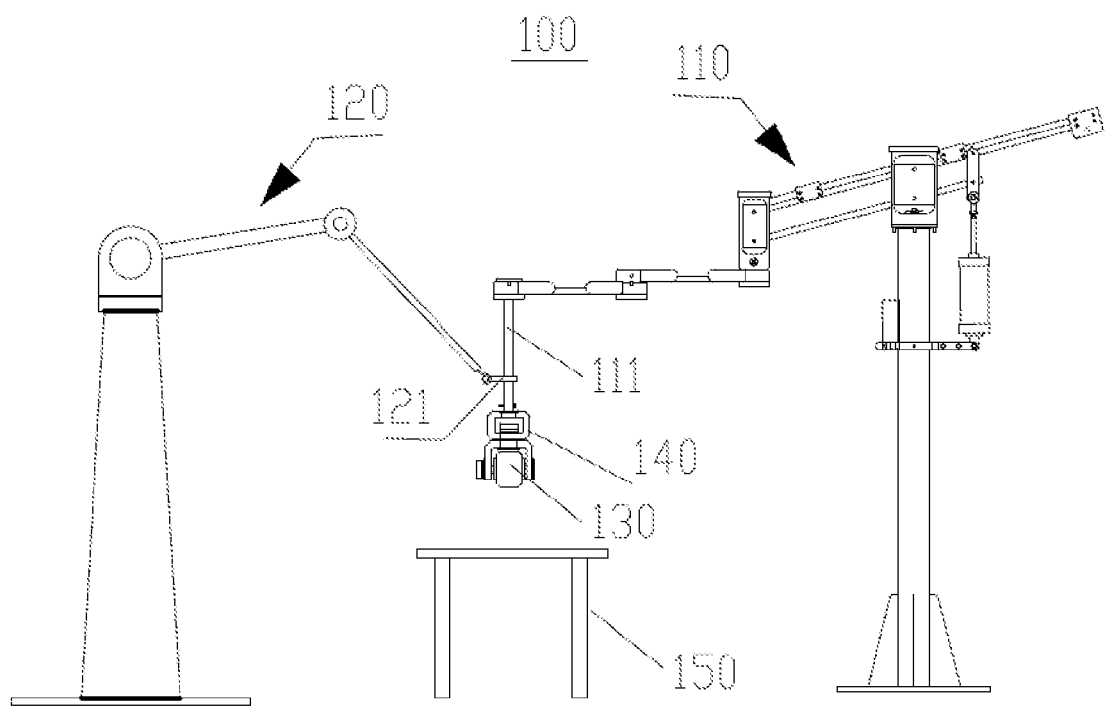
FIG. 1 shows a schematic view of a control system for a capsule endoscope.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Referring to FIG. 1, which shows a schematic view of a control system for a capsule endoscope. As shown in FIG. 1, the control system for the capsule endoscope 100 comprises a balance arm device 110, a mechanical arm 120, a permanent magnet 130 and a 2-DOF rotary platform 140. The bottom of the balance arm device 110 is fixed, and the active end of the balance arm device 110 connects with a boom 111. The bottom of the mechanical arm 120 is fixed and the active end of the mechanical arm 120 connects with a spherical hinge 121. The spherical hinge 121 connects to the boom 111, and assists the boom 111 to move in all directions above and at the side of the subject to be examined for accurate positioning. The 2-DOF rotary platform 140 is linked below the boom 111 and the permanent magnet 130 is located in the 2-DOF rotary platform 140. An examination bed 150 is put below the 2-DOF rotary platform 140 for convenient examination of the subject lying on the bed. The area between the examination bed 150 and the 2-DOF rotary platform 140 is an examination area. At the time of examination, the capsule endoscope containing a small magnet enters the digestive tract of the subject, and with the assistance of the balance arm device 110 and the mechanical arm 120, the permanent magnet 130 acts on the small magnet inside the capsule endoscope to drive the capsule endoscope to move within the digestive tract.

In the embodiment, the control system 100 further comprises a console (not shown in FIG. 1) which is used to drive the mechanical arm 120 to move to adjust spatial positions of the boom 111, so as to drive the permanent magnet 130 to move in three-dimensional space. The console is also used to detect and obtain the spatial positions of the permanent magnet 130, and the spatial positions of the permanent magnet 130 comprise a three-dimensional position and a two-dimensional direction.

In another embodiment, the control system 100 does not comprise a console. The mechanical arm 120 is manually moved to adjust the spatial positions of the boom 111, so as to drive the permanent magnet 130 to move in three-dimensional space. In such case, the control system 100 can comprise a magnetic sensor array (not shown in FIG. 1). The magnetic sensor array comprises a plurality of magnetic sensors that are used to detect the spatial positions of the permanent magnet 130.

In the embodiment, the permanent magnet 130 performs two-dimensional rotation within the 2-DOF rotary platform 140. At this moment, it is necessary to make sure that the initial direction of the rotary platform 140 is unchanged. When the balance arm device 110 and the mechanical arm 120 adjust the spatial positions, the 2-DOF rotary platform 140 may have a deflection and the angle of deflection can be superimposed on the rotation angle of the permanent magnet 130. In order to improve the control precision of the permanent magnet 130 on the capsule endoscope, the angle of deflection of the 2-DOF rotary platform 140 needs to be compensated.

Figure 10:
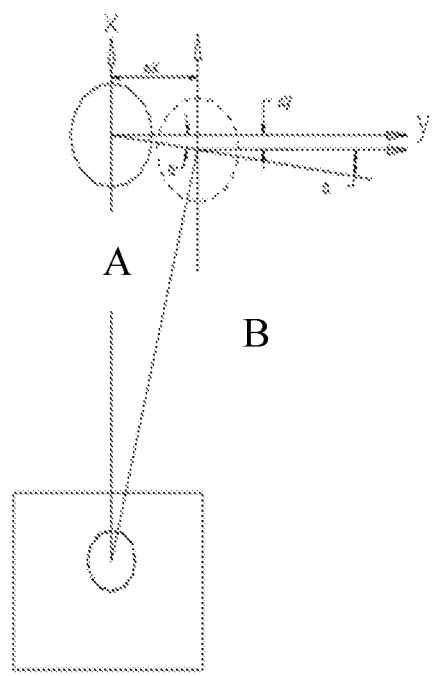
FIG. 10 shows a schematic view of calculating a compensation angle of the 2-DOF rotary platform according to displacement of the permanent magnet.

In the embodiment, the console or the magnetic sensor array detects the position and direction of the permanent magnet 130, and calculates the compensation angle of the 2-DOF rotary platform 140 according to the displacement of the permanent magnet 130. As shown in FIG. 10, the permanent magnet 130 and the 2-DOF rotary platform 140 are moved from position A to position B, the displacements of the permanent magnet 130 in the x and y directions are Δx and Δy, and the compensation angle α of the 2-DOF rotary platform 140 is calculated as $$\tan \alpha = \frac{\Delta y}{\Delta x}.$$

In the embodiment, the 2-DOF rotary platform 140 and the permanent magnet 130 are located at the end of the balance arm device 110 and the mechanical arm 120. When the 2-DOF rotary platform 140 is moved horizontally, the permanent magnet 130 has a deflection to the geodetic coordinate system. To prevent the permanent magnet 130 from deflection to the geodetic coordinate system, the horizontal deflection angle of the permanent magnet 130 is compensated. When the magnetic sensor array detects a certain horizontal movement direction of the permanent magnet 130, the horizontal orientation of the magnet NS pole should be consistent with the horizontal movement direction. At this time, the permanent magnet 130 will rotate from the original horizontal angle to the movement direction angle, and during rotation, the deflection of the permanent magnet 130 to the geodetic coordinate system is compensated. The compensated deflection angle of the permanent magnet 130 is a negative deflection angle of the 2-DOF rotary platform 140.

When the capsule endoscope is at the lower gastric wall of the subject, the tangential direction of the permanent magnet 130 rotating away from the lower gastric wall is opposite to the movement direction of the permanent magnet 130. When the capsule endoscope is at the upper gastric wall of the subject, the tangential direction of the permanent magnet 130 rotating away from the upper gastric wall is consistent with the movement direction of the permanent magnet 130. The speed of rotation and movement of the permanent magnet 130 follows: v=ω*L, wherein v is the average movement speed of the permanent magnet 130, ω is the average rotation angular speed of the permanent magnet 130, and L is the length of the capsule endoscope.

Figure 11:
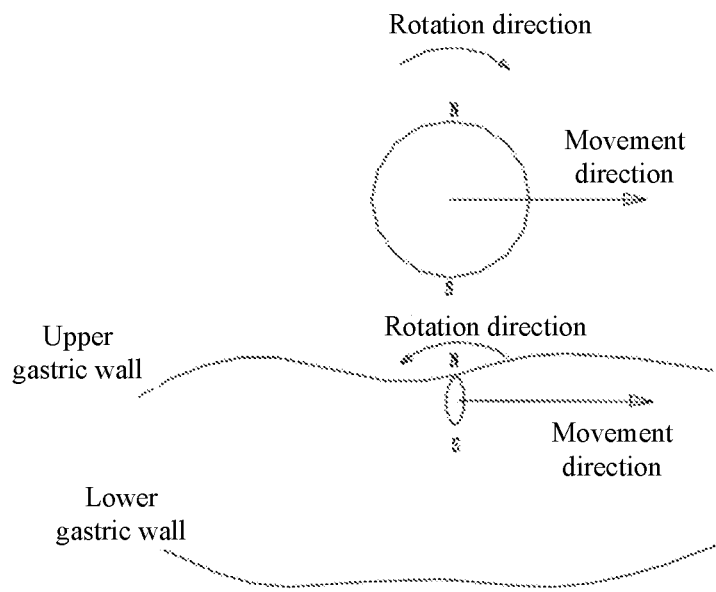
FIGS. 11 and 12 show schematic views of movement of the capsule endoscope at the upper gastric wall under the control of the permanent magnet rotating and moving.
Figure 12:
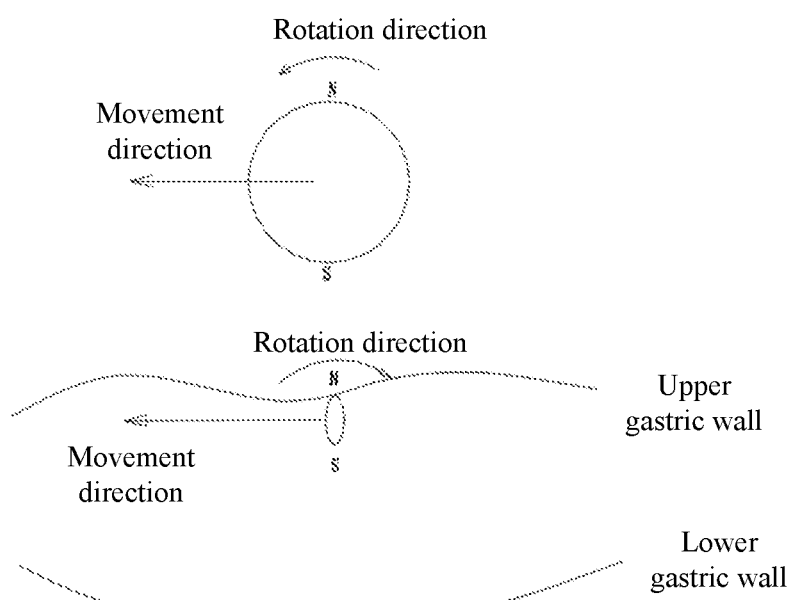

Referring to FIGS. 11 and 12, which show schematic views of movement of the capsule endoscope at the upper gastric wall under the control of the permanent magnet 130 rotating and moving. As shown in FIG. 11, when the permanent magnet 130 moves to the right and rotates to the right (clockwise), the capsule endoscope moves to the right and rotates to the left (counterclockwise. As shown in FIG. 12, when the permanent magnet 130 moves to the left and rotates to the left (counterclockwise), the capsule endoscope moves to the left and rotates to the right (clockwise). That is, the movement direction of the capsule endoscope coincides with the movement direction of the permanent magnet 130, and the rotation direction of the capsule endoscope is opposite to the rotation direction of the permanent magnet 130.

Figure 13:
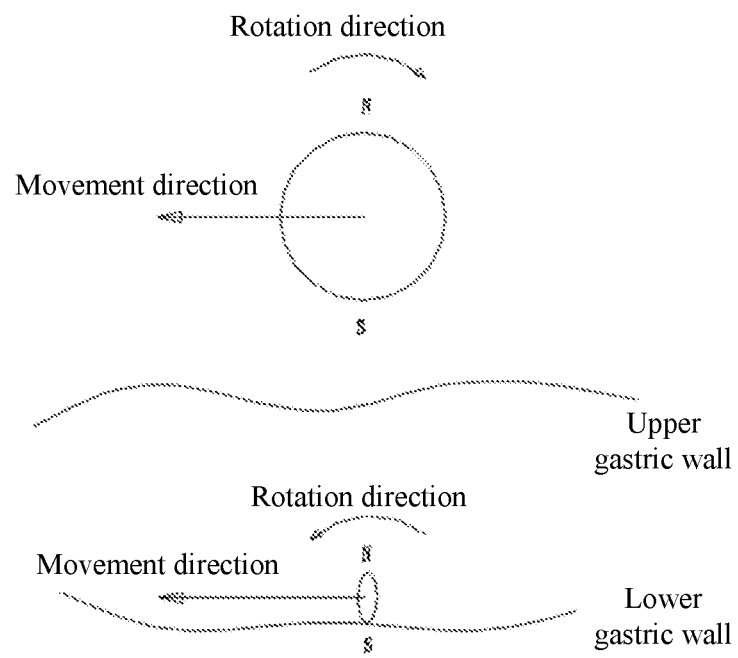
FIGS. 13 and 14 show schematic views of movement of the capsule endoscope at the lower gastric wall under the control of the permanent rotating and moving.
Figure 14:
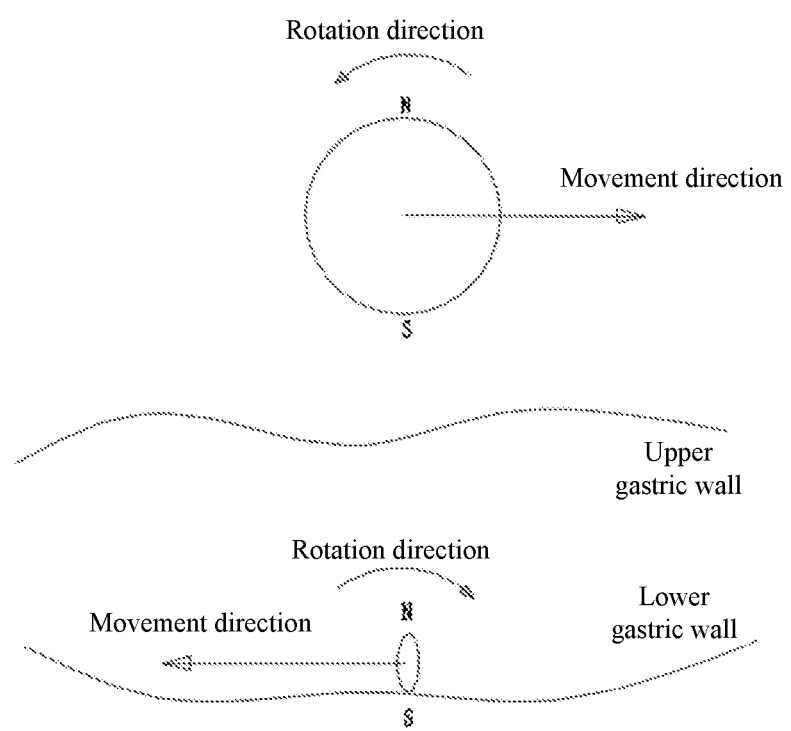

Referring to FIGS. 13 and 14, which show schematic views of movement of the capsule endoscope at the lower gastric wall under the control of the permanent magnet 130 rotating and moving. As shown in FIG. 13, when the permanent magnet 130 moves to the left and rotates to the right (clockwise), the capsule endoscope moves to the left and rotates to the left (counterclockwise). As shown in FIG. 14, when the permanent magnet 130 moves to the right and rotates to the left (counterclockwise), the capsule endoscope moves to the left and rotates to the right (clockwise). That is, the rotation direction of the capsule endoscope is opposite to the rotation direction of the permanent magnet 130.

In the present invention, the balance arm device 110 that works with the mechanical arm 120 to control the 2-DOF rotary t platform 140 to drive the permanent magnet 130 to reach the spatial positions and rotate horizontally and vertically, thus driving the capsule endoscope to implement various movements. Main cost of the mechanical arm 120 is the high-precision motor that withstands large loads. Because of the advantage of the balance arm device 110 that ensures balance of gravity during the whole examination process, the load bearing requirement for the mechanical arm 120 is greatly reduced, and thereby the cost of the mechanical arm 120 can be dramatically lowered. Together with the advantages of the mechanical arm 120 that achieves accurate movement and positioning in the spatial positions, low cost and high accuracy of the entire control system 100 can be achieved.

Figure 2:
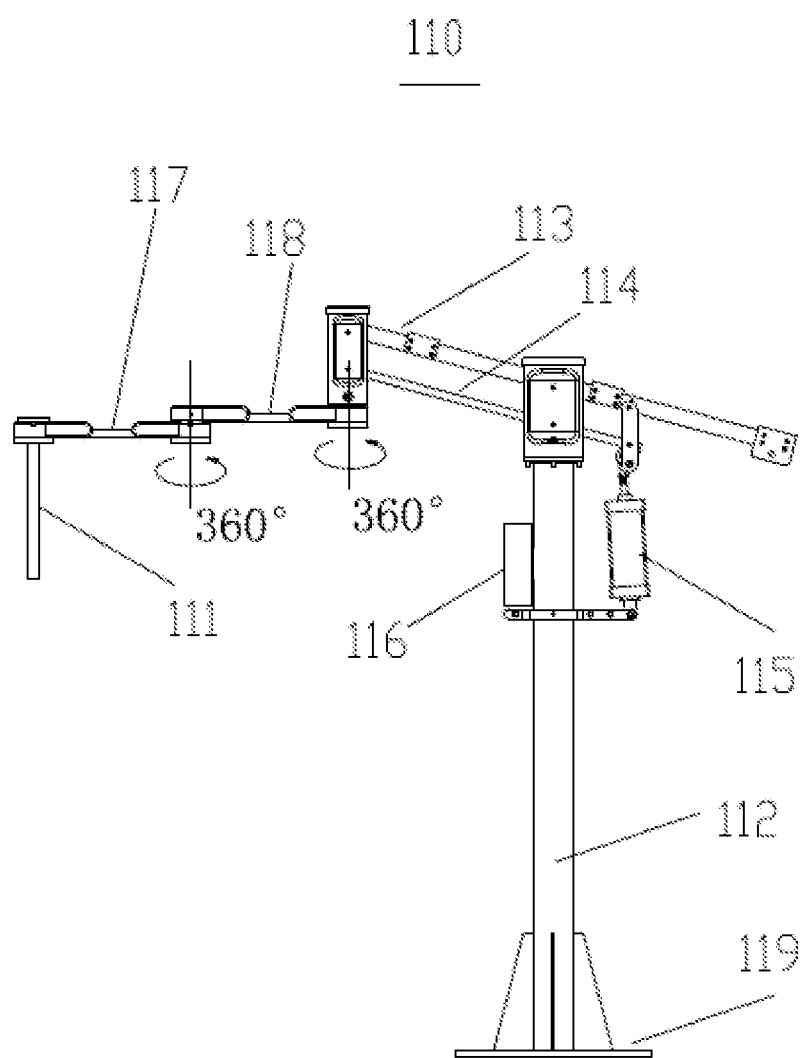
FIG. 2 shows a schematic view of a pneumatic balance arm of FIG. 1.
Figure 15:
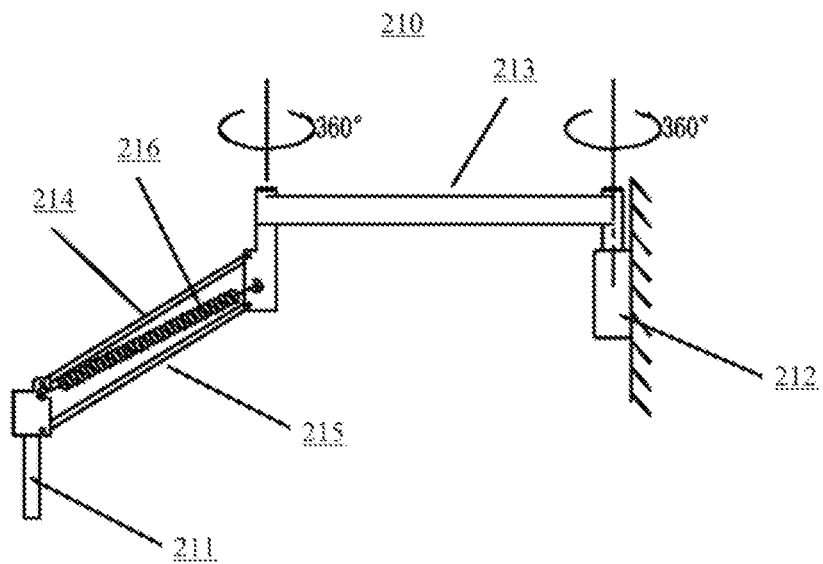
FIG. 15 shows a schematic view of a spring assisted balance arm.
Figure 16:
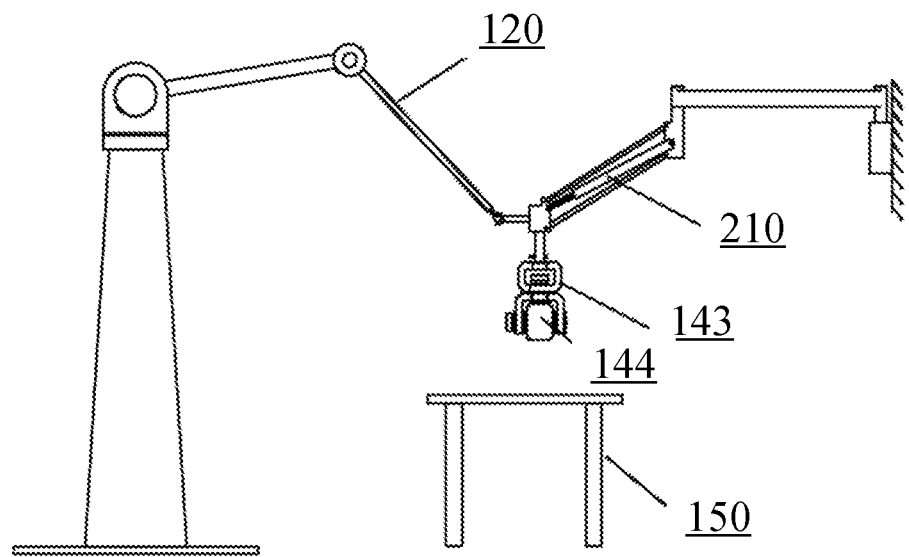
FIGS. 16, 17, 18, and 19 show schematic views of the control system which the balance arm device and the mechanical arm are in a split structure.
Figure 19:
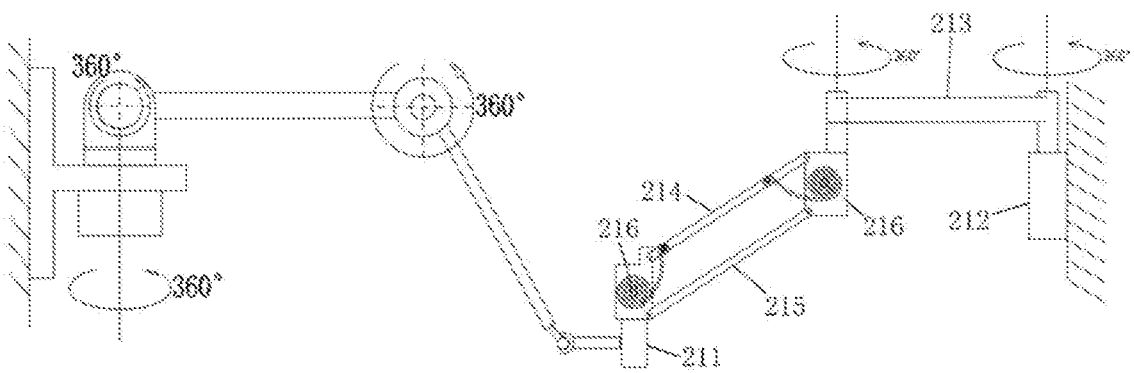
Figure 20:
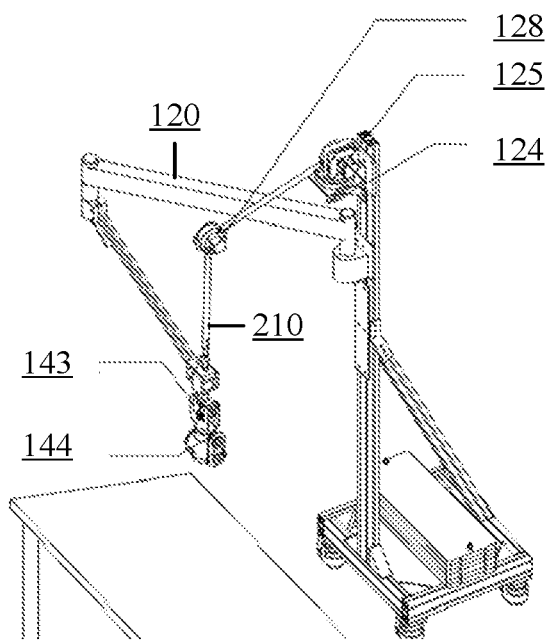
FIG. 20 show a schematic view of the control system which the balance arm device and the mechanical arm are in an integrated structure.

The balance arm device 110 can be a pneumatic balance arm 110 that uses a balance cylinder 115 to balance the boom 111, as shown in FIG. 2, or can be a spring assisted balance arm 210 that uses a common spring, a coil spring or a gas spring to balance the boom 111, as shown in FIG. 15, FIG. 16 or FIG. 19.

FIG. 2 shows a schematic view of the pneumatic balance arm 110 of FIG. 1.

The pneumatic balance arm 110 comprises a column 112 and a chassis 119 for providing support. A upper balance arm 113 and a lower balance arm 114 that are parallel to each other and have an angle to the column 112 are attached to the top of the column 112; the balance cylinder 115 is fixed on a side of the column 112 through a hinge and is located below the upper balance arm 113 and the lower balance arm 114, a tracheal piston of the balance cylinder 115 is connected to the upper balance arm 113 and the lower balance arm 114 through a hinge for providing impetus for the upper balance arm 113 and the lower balance arm 114 moving upward or downward. Under the telescopic pull of tracheal piston action of the balance cylinder 115, the upper balance arm 113 and the lower balance arm 114 can deflect 360 degrees vertically and horizontally. That is, when the tracheal piston of the balance cylinder 115 contracts, the upper balance arm 113 and the lower balance arm 114 are tilted up, and when the tracheal piston of the balance cylinder 115 is stretched, the upper balance arm 113 and the lower balance arm 114 are lowered.

The other ends of the upper balance arm 113 and the lower balance arm 114 are connected to the rear terminal arm 118 and the front terminal arm 117. The rear terminal arm 118 is located between the front terminal arm 117 and the upper balance arm 113 and lower balance arm 114. Wherein, the rear terminal arm 118 is pivotally connected to the upper balance arm 113 and the lower balance arm 114, and the rear terminal arm 118 can rotate horizontally 360 degrees along the pivot. The front terminal arm 117 and the rear terminal arm 118 are also pivotally connected, and the front terminal arm 117 can rotate horizontally 360 degrees along the pivot. Specifically, the rear terminal arm 118 or the front terminal arm 117 can be driven to rotate horizontally 360 degrees along the axis, by a human arm or mechanical arm. The boom 111 is perpendicularly connected to the other end of the front terminal arm 117. In the embodiment, the upper balance arm 113, the lower balance arm 114, the rear terminal arm 118, and the front terminal arm 117 are both rigid arms.

In the embodiment, the balance arm device 110 is used to balance the load weight, to reduce the force demand on the man power or the mechanical arm motor.

A control box 116 is also fixed on other side of the column 112. The control box 116 is electrically connected to the balance cylinder 115 for controlling the cylinder piston to move up and down. Under the control of the control box 116, the piston of the balance cylinder 115 moves up and down to drive the upper balance arm 113 and the lower balance arm 114 to move up and down in the vertical direction, and finally drive the boom 111 to move up and down. In this way, the rigid arm of the pneumatic balance arm 110 can bear the weight of the permanent magnet 130 fixed at the end of the boom 111 and overcome the gravity to move the permanent magnet 130 up and down, left and right, and achieve gravity balancing.

The chassis 119 can either be the fixed chassis shown in FIG. 2, or a movable chassis (not shown in FIG. 2) with wheels on the bottom. The wheels of the movable chassis can be moved and locked. A balance weight object can be configured on the movable chassis to balance the weight of the control system 100, so as to avoid that the movable chassis cannot be fixed because of too large weight of the permanent magnet 130.

In one embodiment, when the control system 100 comprises the magnetic sensor array, the magnetic sensor array is fixed on the column 112.

Figure 3:
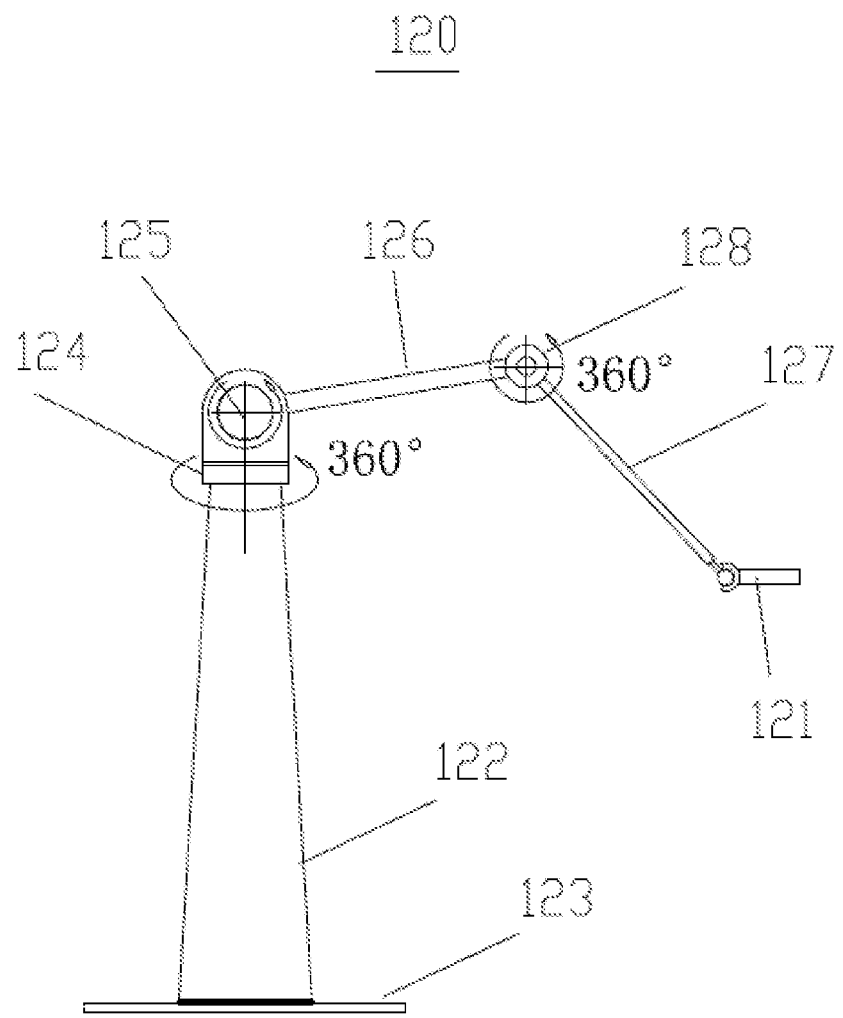
FIG. 3 shows a schematic view of a mechanical arm of FIG. 1.

FIG. 3 shows a schematic view of the mechanical arm 120 of FIG. 1. The mechanical arm 120 comprises a spherical hinge 121 connected to the boom 111 of the pneumatic balance arm 110. The mechanical arm 120 further comprises a column 122 and a chassis 123 for support purpose. The top of the column 122 has a first motor 124 and a second motor 125 fitted. A rear arm 126 is connected to the second motor 125. The first motor 124 is used to drive the second motor 125 and the rear arm 126 to rotate in horizontal direction parallel to the chassis 123, and the second motor 125 drives the rear arm 126 to rotate in vertical direction. The mechanical arm 120 further comprises a third motor 128 and a front arm 127. The other end of the rear arm 126 is connected to the front arm 127 through the third motor 128, and the third motor 128 can drive the front arm 127 to rotate 360 degrees. The other end of the front arm 127 is connected to the spherical hinge 121. In the embodiment, the movement of the mechanical arm 120 is driven by the first motor 124, the second motor 125 and the third motor 128.

Figure 22:
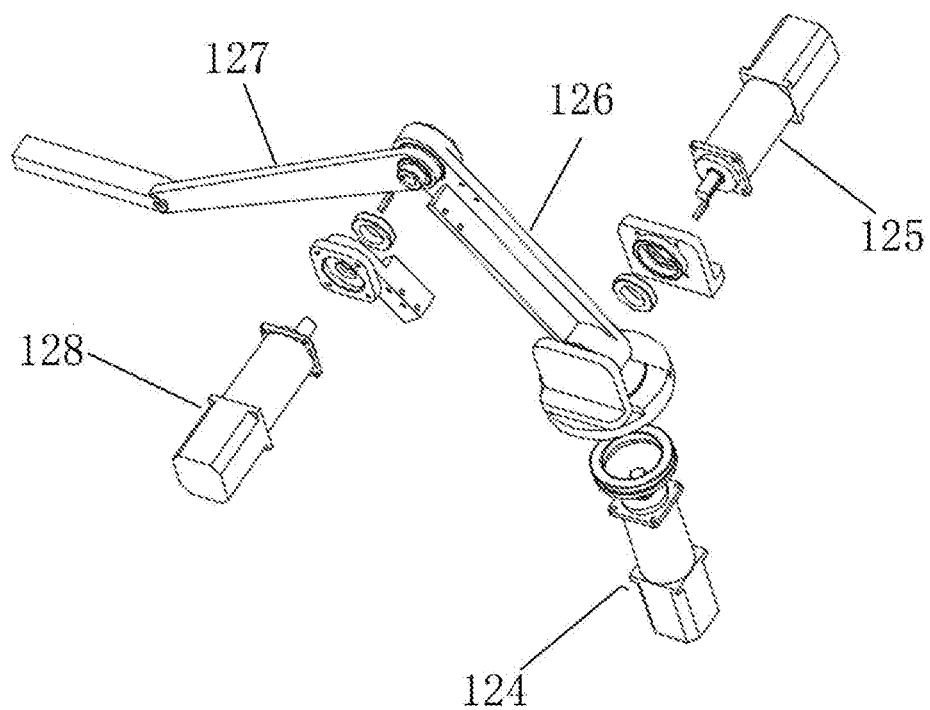
FIGS. 22 and 23 are views showing connection structure of the first motor, the second motor and the third motor.
Figure 23:
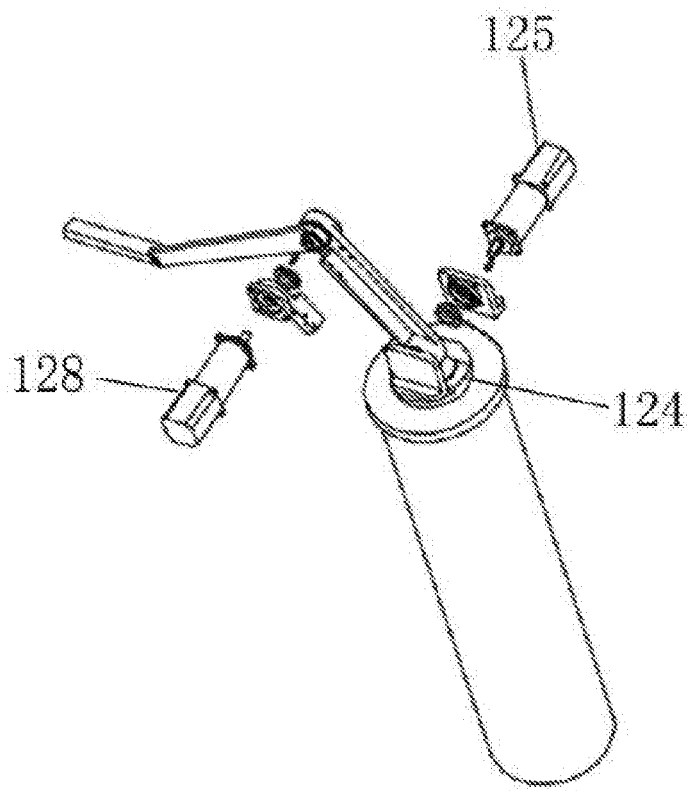

Specifically, as shown in FIG. 22 and FIG. 23, the first motor 124 is fixed in the column 122, and the output shaft of the first motor 124 is connected to the second motor 125. The second motor 125 is fixed to the column 122 through a motor bracket, and the output shaft of the second motor 125 is coupled to the rear arm 126 through a bearing. The third motor 128 is fixed to the rear arm 126 by a motor bracket, and the output shaft of the third motor 128 is coupled to the front arm 127.

The chassis 123 can either be the fixed chassis shown in FIG. 3, or a movable chassis (not shown in FIG. 3) provided with casters on the bottom. The casters of the movable chassis can be moved and locked. A balance weight can be configured on the movable chassis to balance the weight of the control system 100, so as to avoid that the movable chassis cannot be fixed because of too large weight of the mechanical arm 120.

In another embodiment, a base can be used to replace the column 122 and the chassis 123. The bottom of the base is fixed, the base can either be wall-mounted that is fixed on a wall surface or ceiling-mounted that is hung and fixed on a ceiling. The first motor 124 and the second motor 125 are fitted on the top of the base.

Figure 21:
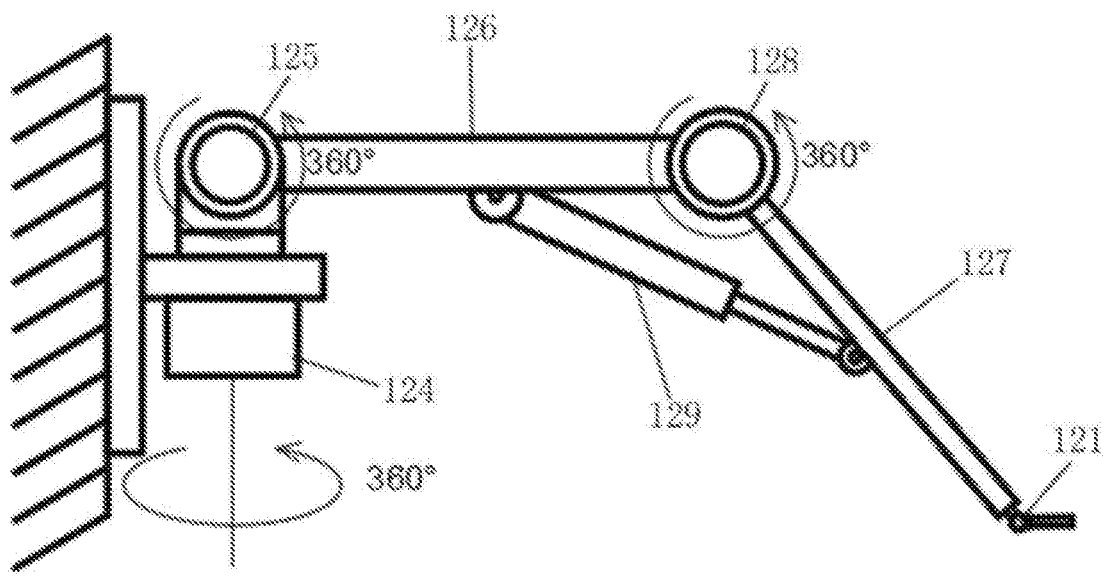
FIG. 21 is a schematic view showing the structure of the mechanical arm provided with a gas spring.

In other embodiments, the mechanical arm 120 further includes a gas spring 129 connected to the front arm 127. The gas spring 129 is fixedly disposed on the rear arm 126. The piston rod of the gas spring 129 is coupled to the front arm 127 for driving the front arm 127 moving up and down to reduce the output requirement of the third motor 128, as shown in FIG. 21. It can be understood that in other embodiments, the gas spring 129 can also be fixedly disposed on other suitable components as long as the movable end thereof is coupled to the front arm 127 and can drive the front arm 127 to move.

Figure 4:
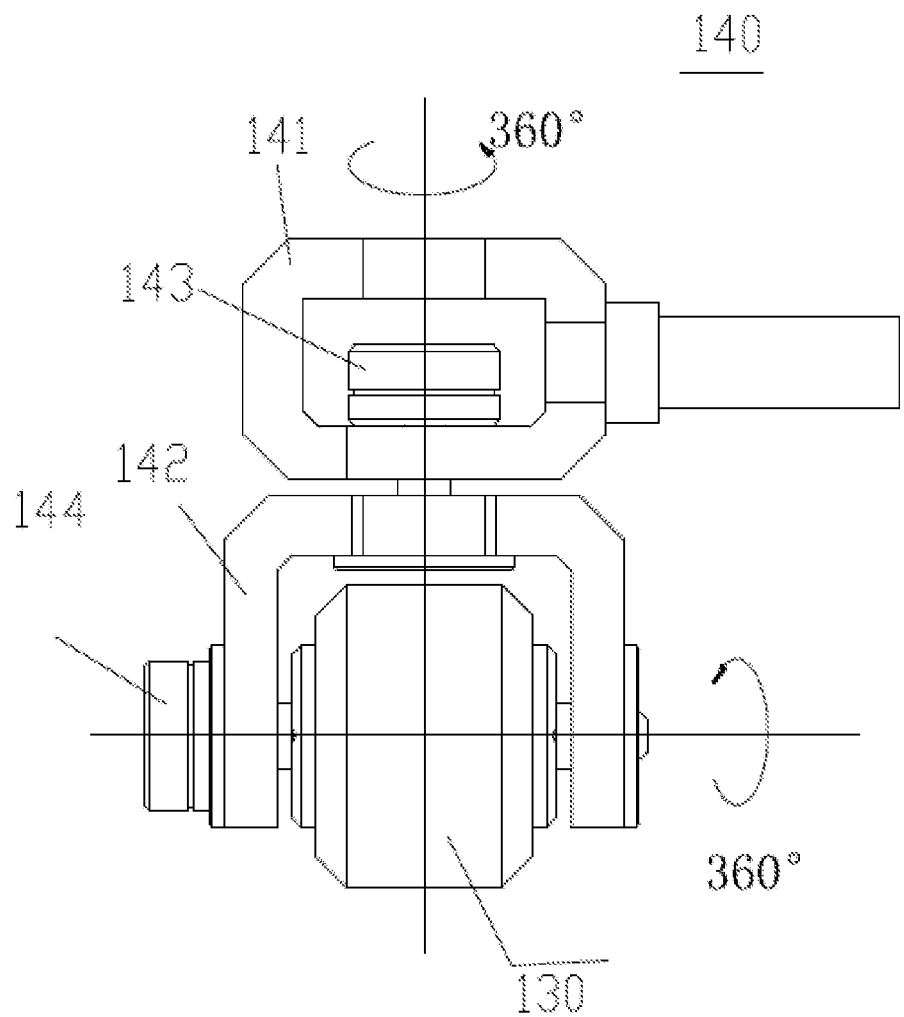
FIG. 4 shows a schematic view of a 2-DOF rotary platform of FIG. 1.

FIG. 4 shows a schematic view of the 2-DOF rotary platform 140 of FIG. 1. The 2-DOF rotary platform 140 is an electrically controlled rotary platform, comprising a first enclosure 141 and a second enclosure 142 that are connected to each other. The first enclosure 141 has a fourth motor 143 therein which provides a 360-degree rotation along the longitudinal axis; the second enclosure 142 has a fifth motor 144 therein which provides a 360-degree rotation along the horizontal axis. The compensation angle α of the 2-DOF rotary platform 140 is automatically compensated by the fifth motor 144.

Figure 24:
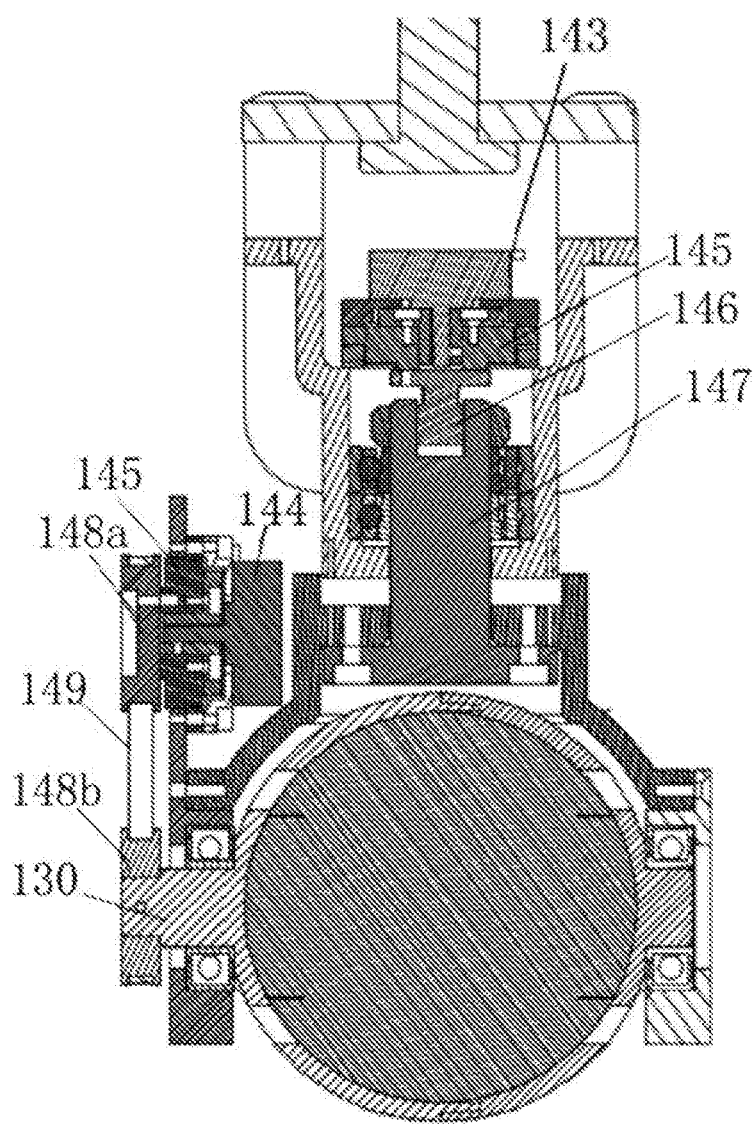
FIG. 24 is a view showing an examplar connection structure of the fourth motor and the fifth motor.

As shown in FIG. 24, the fourth motor 143 is connected to one end of the main shaft 147 via the harmonic reducer 145 and the coupling 146, and the other end of the main shaft 147 is connected to the second enclosure 142, and then passes through the fourth motor 143. The second enclosure 142 is driven to rotate 360 degrees in the longitudinal direction. The fifth motor 144 is connected to the permanent magnet 130 via the harmonic reducer 145, the synchronous wheel and the timing belt 149, and further drives the permanent magnet 130 to rotate 360 degrees in the horizontal axis direction by the fifth motor 144. Among them, the synchronous wheel includes a primary synchronous wheel 148a and a secondary synchronous wheel 148b.

In this way, the fifth motor 144 driving the 2-DOF rotary platform 140 to rotate horizontally and the fourth motor 143 driving the 2-DOF rotary platform 140 to rotate vertically are used to achieve 2-DOF rotating and positioning of the permanent magnet 130. The mechanical arm 120 works with the pneumatic balance arm 110 to drive the permanent magnet 130 connected to the boom 111 to move in a three-dimensional space, thereby driving the permanent magnet 130 to move in five degrees of freedom.

Before use, adjust the 2-DOF rotary platform 140, the examination bed 150, and the control box 116 to be as horizontal as possible. Specifically, the maximum allowable ground levelness of the 2-DOF rotary platform 140 and the examination bed 150 is ±2.5 mm, and the ground undulation is within the allowable range of a levelness; the maximum allowable ground levelness of the control box 116 is 5 mm, and the ground undulation is within the allowable range of z levelness; the maximum allowable levelness of other unit is ±10 mm.

Figure 5:
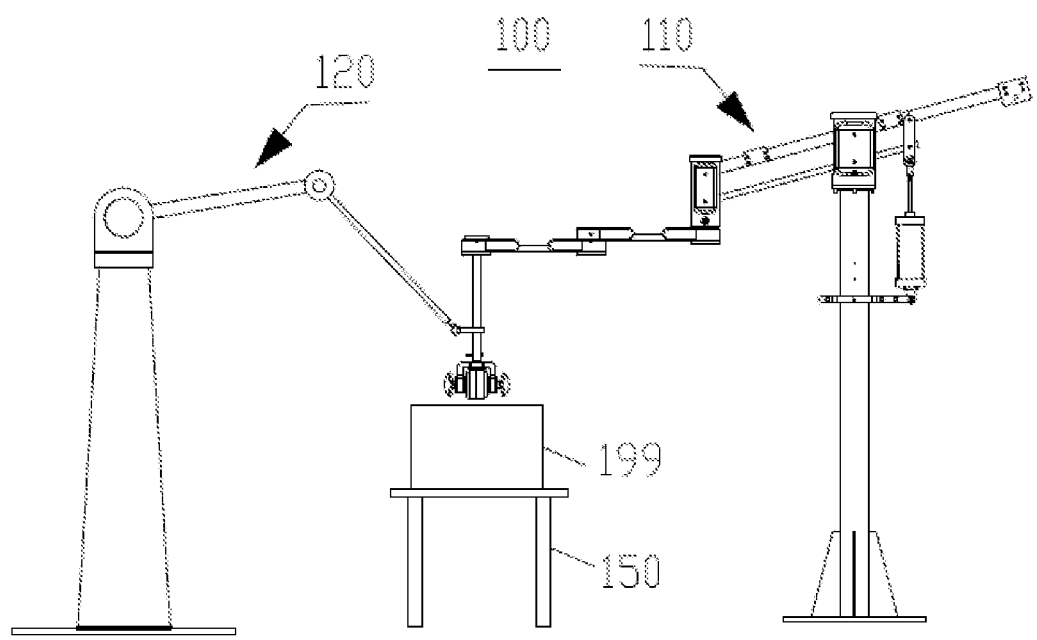
FIG. 5 shows a schematic view of the status of the control system in use.

FIG. 5 shows a schematic view of the status of the control system for the capsule endoscope 100 in use. As shown in FIG. 5, in operation, the height of the examination bed 150 is H0, and the area 199 above the examination bed 150 is the lying area for the subject, and the height of the area is H1. Above the area 199 is the movement area of the 2-DOF rotary platform 140 and the permanent magnet 130.

Figure 6:
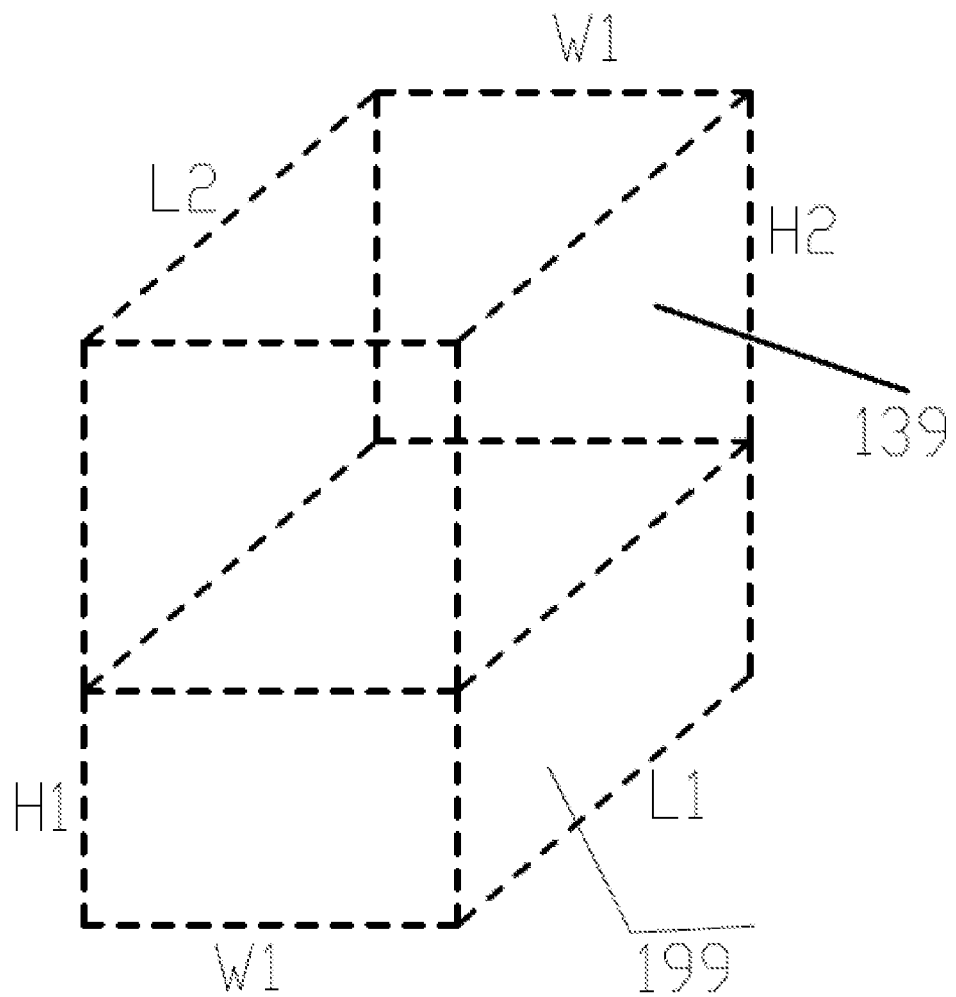
FIG. 6 shows a schematic view of a movement area of a permanent magnet above a subject under the control of the pneumatic balance arm.

FIG. 6 shows a schematic view of the movement area of the permanent magnet 130 above the subject under the control of the pneumatic balance arm 110. At this time, the movement area 139 of the permanent magnet 130 is above the area 199 where the subject is located, as shown in FIG. 6. The length of the digestive tract L1, the digestive tract width W1, and the digestive tract height H1 of the subject to be examined can be seen in FIG. 6. The width W2 of the movement range 139 of the permanent magnet 130 is substantially equal to the width W1 of the digestive tract, the length L2 of the movement range 139 is equivalent to the length L1 of the digestive tract, and the height H2 of the movement range 139 is the distance from the human body to a point where the capsule endoscope in digestive tract is out of control of the permanent magnet 130.

Figure 7:
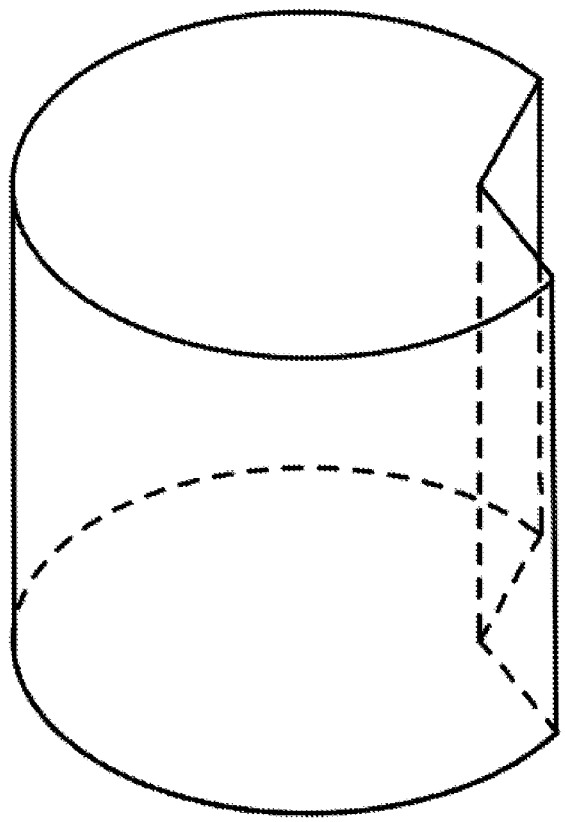
FIG. 7 shows a schematic view of an effective reachable area of the permanent magnet under the combined action of the pneumatic balance arm and the mechanical arm, as examined from one side of the subject.

In one embodiment, FIG. 7 shows a schematic view of the effective reachable area of the permanent magnet under the combined action of the pneumatic balance arm 110 and the mechanical arm 120, as examined from one side of the subject. Wherein, in one implementation, the triangular area is an area the permanent magnet can not reach. As shown in FIG. 7, under the combined action of the pneumatic balance arm 110 and the mechanical arm 120, the permanent magnet 130 can reach the omni-directional area around the human digestive tract. Compared to the prior art, the examinable area has been significantly expanded, which is conducive to improving the examination accuracy and range.

Figure 8:
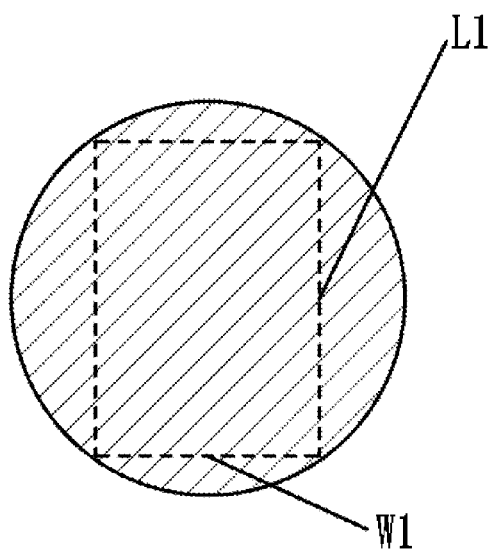
FIG. 8 shows a schematic view of the effective reachable area of the permanent magnet as examined from above of the subject.

In another embodiment, FIG. 8 shows a schematic view of the effective reachable area of the permanent magnet as examined from above the subject. As shown in FIG. 8, the rectangular area is a planar area formed by the digestive tract length L1 and the width W1 of the subject to be examined. The shaded area including both the circular area and the rectangular area is the effective reachable area of the permanent magnet.

Figure 9:
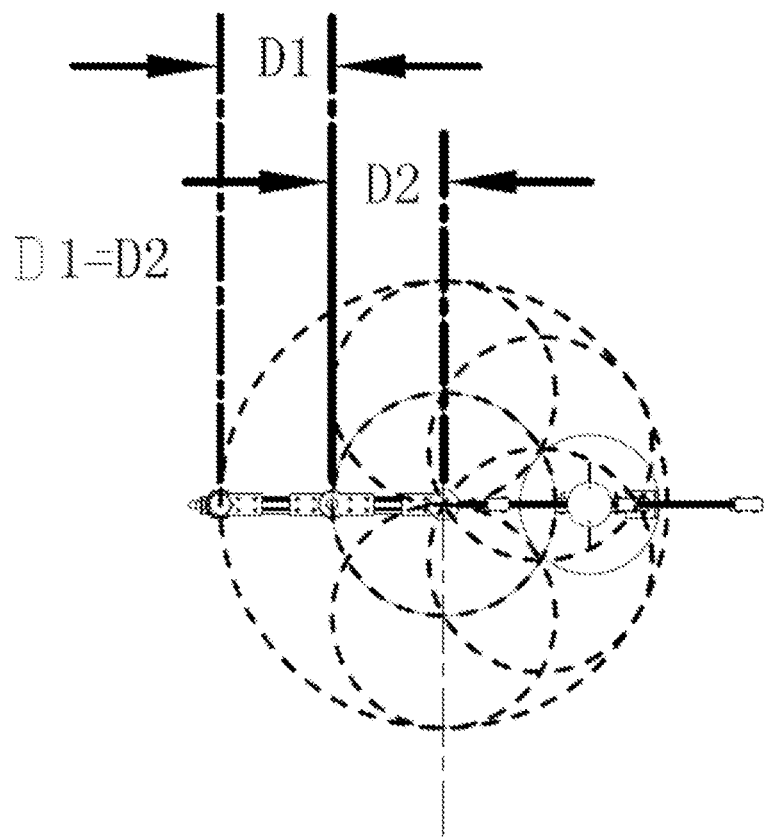
FIG. 9 shows a top schematic view of the effective reachable area of the permanent magnet.

In still another embodiment, FIG. 9 shows a top schematic view of the effective reachable area of the permanent magnet. As shown in FIG. 9, the outer large circular area is the effective arrival area of the permanent magnet, and each small circle is the area that the permanent magnet can be detected when the permanent magnet moves to each detection area. Therefore, the permanent magnet 130 can expand detection range of the digestive tract under the action of the pneumatic balance arm 110 and the mechanical arm 120.

FIG. 15 shows a schematic view of the spring assisted balance arm 210. The spring assisted balance arm 210 comprises a base 212 for providing support. The base has its bottom fixed, and can be wall-mounted that is fixed on a wall surface (as shown in FIG. 15), or ceiling-mounted that is hung and fixed on a ceiling (not shown in FIG. 15). The spring assisted balance arm 210 further comprises a horizontal swing arm 213 connected to the top of the base. The other end of the horizontal swing arm 213 is connected with an upper balance arm 214, a lower balance arm 215, and a spring 216 that are angled with the horizontal swing arm 213. The upper balance arm 214 and the lower balance arm 215 are parallel to each other, and the spring 216 is used to provide impetus for the upper balance arm 214 and the lower balance arm 215 to move upward or downward through deformation thereof. Under the action of the spring 216, the upper balance arm 214 and the lower balance arm 215 can move 360 degrees vertically and horizontally. The spring 216 may be a common spring, a coil spring or a gas spring.

Figure 25:
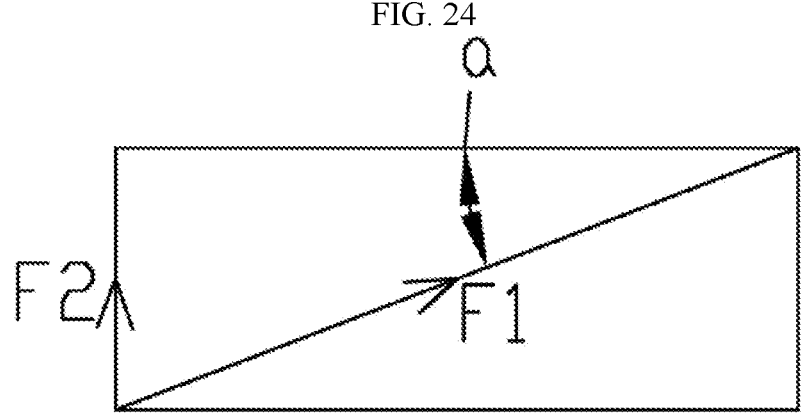
FIG. 25 is a schematic view showing a direction of a force generated by the deformation of a spring.

In the present application, the common spring, the coil spring or the gas spring are used to balance the load and reduce the force demand on the man power or the mechanical arm motor. As shown in FIG. 25, after the springs are deformed, spring forces F1 and F2 are generated in two directions. The spring forces F1 and F2 act on the upper balance arm and the lower balance arm, F2=sin α×F1, in common, F2 is used for balance for the load.

In other embodiment, a column is used to replace the base 212 for providing support to the spring assisted balance arm 210, and the bottom of the chassis can be a fixed chassis or a movable chassis provided with casters on the bottom.

Wherein, the horizontal swing arm 213 is pivotally connected to the base 212, and is also pivotally connected to the upper balance arm 214 and the lower balance arm 215. The horizontal swing arm 213 can rotate 360 degrees horizontally along the pivot. The boom 211 is vertically connected to the other end of the upper balance arm 214, the lower balance arm 215 and the spring 216. In the embodiment, the upper balance arm 214, the lower balance arm 215, and the horizontal swing arm 213 are all rigid arms.

In this way, the rigid arm of the spring assisted balance arm 210 can bear the weight of the permanent magnet 130 fixed at the end of the boom 211 and overcome the gravity to move the permanent magnet 130 up and down, left and right, and achieve gravity balancing.

When the control system comprise the magnetic sensor array, the mounting position of the magnetic sensor array is determined based on the mounting position of the base 212. When the base 212 is wall-mounted, the magnetic sensor array is also mounted on the wall surface near the base 212. When the base 212 is ceiling-mounted, the magnetic sensor array is also mounted on the ceiling near the base 212.

Figure 17:
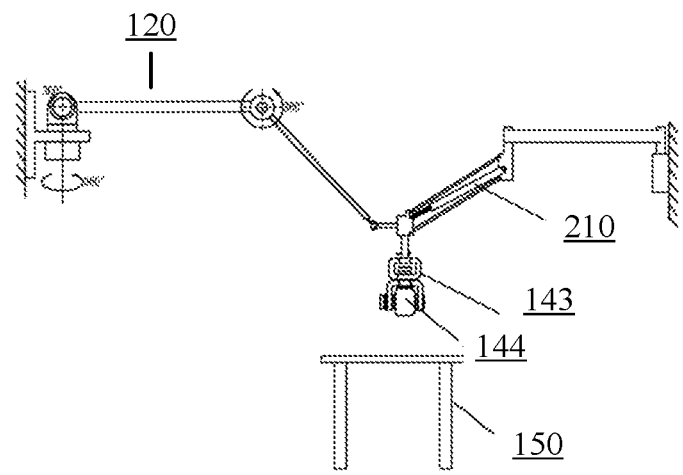
Figure 18:
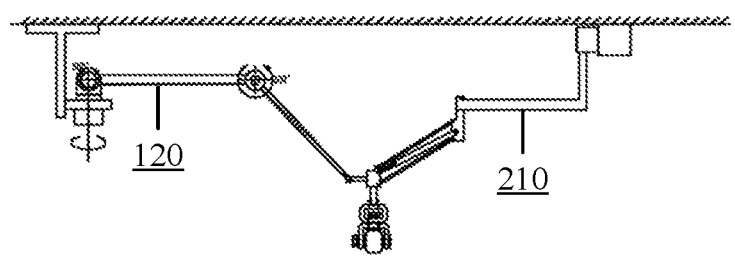

In the embodiment, the balance arm device 110 and the mechanical arm 120 are in a split structure. That is, the balance arm device 110 and the mechanical arm 120 are fixed to different fixing objects. The balance arm device 110 can be a pneumatic balance arm 110 or a spring assisted balance arm 210. Under the premise of different fixing objects, the pneumatic balance arm 110 can be fixed to a column, and the spring assisted balance arm 210 and the mechanical arm 120 can be fixed to a column, a base mounted on a wall surface or a base mounted on a ceiling. The chassis of the column can be a fixed chassis or a movable chassis with wheels on the bottom. As shown in FIG. 1, the pneumatic balance arm 110 and the mechanical arm 120 are fixed to different columns. As shown in FIG. 16, the spring assisted balance arm 210 is fixed to a base mounted on a wall surface and the mechanical arm 120 is fixed to a column. As shown in FIG. 17, the spring assisted balance arm 210 and the mechanical arm 120 are fixed to different bases mounted on different places of a wall surface. As shown in FIG. 18, the spring assisted balance arm 210 and the mechanical arm 120 are fixed to different bases mounted on different places of a ceiling.

In other embodiment, the balance arm device 110 and the mechanical arm 120 are in an integrated structure. That is, the balance arm device 110 and the mechanical arm 120 are fixed to a same fixing object. The balance arm device 110 can be a pneumatic balance arm 110 or a spring assisted balance arm 210. Under the premise of same fixing object, the pneumatic balance arm 110 can be fixed to a column, and the spring assisted balance arm 210 and the mechanical arm 120 can be fixed to a column, a base mounted on a wall surface or a base mounted on a ceiling. The chassis of the column can be a fixed chassis or a movable chassis with wheels on the bottom. As shown in FIG. 19, the spring assisted balance arm 210 and the mechanical arm 120 are fixed to a same column, and the column is a movable chassis with wheels on the bottom.

Compared to the prior art, in the present invention, firstly, the main load carried by the mechanical arm 120 is heavy high-precision motors (the first motor, the second motor and the third motor), and the gravity of the 2-DOF rotary platform 140 and the permanent magnet 130 is entirely supported by the balance arm device 110, which can greatly reduce the load on the mechanical arm 120, avoid high cost of the motor bearing due to the use of the mechanical arm 120 alone, and thereby substantially lower the cost of precision mechanical arm 120.

Secondly, the present invention provides a balance arm device 110 which solves the vertical and horizontal movement of the permanent magnet 130 in the area above the subject. The mechanical arm 120 can drive the boom 111 of the balancing arm 110 to rotate, thereby driving the permanent magnet 130 to realize accurate positioning with no dead corner in the entire area above the digestive tract of the subject, improving examination accuracy.

Further, the 2-DOF rotary platform 140 drives the permanent magnet 130 to rotate horizontally and vertically, providing a 2-DOF rotation positioning in the horizontal and vertical directions.

As a result, the control system for the capsule endoscope 100 uses a balance arm device in combination with a mechanical arm to control spatial positions of the 2-DOF rotary platform, thus to provide a 5-DOF movement range; the mechanical arm can also achieve accurate moving and positioning in the spatial positions, thereby realizing low-cost and high-precision of the entire control system.

In addition, in combination with the 2-DOF rotary platform, the control system for the capsule endoscope disclosed in the present invention realizes a simple transfer of human-permanent magnet or human-console-permanent magnet, which makes the system simpler, and enables the permanent magnet to move in the area around the subject, more fitting to the human body, so that the control of the capsule endoscope is more direct and effective.

Finally, the balance arm device 110 and the mechanical arm 120 of the present invention are stably placed on the horizontal plane before being put into use, and do not move during use, but rely on the mechanical arm to adjust the position. Therefore, possible collisions caused in the system of the prior art which adjusts the position by means of the device moving around is avoided, 5-DOF movement of the permanent magnet 130 is realized and the effective examination area is expanded.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. A control system for a capsule endoscope, comprising:
a balance arm device, a mechanical arm, a permanent magnet and a 2-DOF rotary platform;
wherein the bottom of the balance arm device is fixed, and an active end of the balance arm device connects with a boom;
wherein the bottom of the mechanical arm is fixed, and an active end of the mechanical arm connects with a spherical hinge;
wherein the 2-DOF rotary platform is fixed below the boom and the permanent magnet is located in the 2-DOF rotary platform;
wherein the spherical hinge connects to the boom, assisting the permanent magnet to move around an area around a subject;
wherein the balance arm device drives the permanent magnet to move up and down, front and back, left and right in an area above a subject to be examined; the mechanical arm drives the boom to rotate;
wherein the mechanical arm comprises an object for providing support, and on the top of the object fixes a first motor, a second motor and a rear arm connected to the second motor; wherein the first motor drives the second motor and the rear arm to rotate in horizontal direction and the second motor drives the rear arm to rotate in vertical direction.

2. The control system of claim 1, further comprising an examination bed, and wherein the examination bed is put below the 2-DOF rotary platform, and the area between the examination bed and the 2-DOF rotary platform is an examination area of the subject.

3. The control system of claim 1, wherein the balance arm device is a pneumatic balance arm, comprising a column and a chassis for support purpose, and the top of the column connects with an upper balance arm and a lower balance arm parallel to each other.

4. The control system of claim 3, wherein the pneumatic balance arm further comprises a balance cylinder and a control box fixed on one side of the column, wherein the control box is electrically connected to the balance cylinder, and the balance cylinder is connected to the upper balance arm and the lower balance arm via a piston; wherein the control box controls the balance cylinder and drives the upper balance arm and the lower balance arm to move in vertical and horizontal directions.

5. The control system of claim 3, wherein the other ends of the upper balance arm and the lower balance arm connects with a rear terminal arm and a front terminal arm, wherein the rear terminal arm is located between the front terminal arm and the upper balance arm and the lower balance arm, wherein the upper balance arm, the lower balance arm, the rear terminal arm and the front terminal arm are rigid arms.

6. The control system of claim 5, wherein the rear terminal arm is pivotally connected to the upper balance arm and the lower balance arm, and the rear terminal arm is rotatable 360 degrees horizontally along a pivot.

7. The control system of claim 5, wherein the front terminal arm is pivotally connected to the rear terminal arm, and the front terminal arm is rotatable 360 degrees horizontally along a pivot.

8. The control system of claim 5, wherein the boom is fixed at the other end of the front terminal arm and is vertically connected to the front terminal arm.

9. The control system of claim 1, wherein the other end of the rear arm connects to the front arm through a third motor, and the third motor drives the front arm to rotate 360 degrees, wherein the spherical hinge is connected to the other end of the front arm.

10. The control system of claim 9, wherein the mechanical arm comprises a gas spring connected to the front arm, and the gas spring drives the front arm moving up and down.

11. The control system of claim 1, wherein the object is a column, and the bottom of the column is a fixed chassis or a movable chassis with wheels on the bottom; or the object a base, and the bottom of the base is fixed on a wall or hanged and fixed on a ceiling.

12. The control system of claim 1, wherein the 2-DOF rotary platform comprises a first enclosure and a second enclosure, a fourth motor fixed in the first enclosure provides a 360-degree rotation along a longitudinal axis, and a fifth motor fixed in the second enclosure provides a 360-degree rotation along a horizontal axis.

13. The control system of claim 1, further comprising a console, wherein the console drives the mechanical arm to move to adjust spatial positions of the boom to drive the permanent magnet to move in three-dimensional space, and the console detects and obtains the spatial positions of the permanent magnet, and the spatial position of the permanent magnet comprises a three-dimensional position and a two-dimensional direction.

14. The control system of claim 1, further comprising a magnetic sensor array, wherein the magnetic sensor array comprises a plurality of magnetic sensors, the magnetic sensor array detect spatial positions of the permanent magnet depends on the magnetic sensors and obtain three-dimensional position and two-dimensional direction of the permanent magnet.

15. The control system of claim 13, wherein a compensation angle of the 2-DOF rotary platform is calculated according to a displacement of the permanent magnet.

16. The control system of claim 13, wherein when the permanent magnet has a horizontal movement direction, the permanent magnet rotates from the original horizontal angle to the movement direction angle, and the deflection of the permanent magnet to the geodetic coordinate system is compensated during rotation.

17. The control system of claim 1, wherein when the 2-DOF rotary platform is moved horizontally, the permanent magnet has a deflection to the geodetic coordinate system, and to prevent the permanent magnet from deflection to the geodetic coordinate system, the horizontal deflection angle of the permanent magnet is compensated.

18. The control system of claim 1, wherein the permanent magnet controls the movement of the capsule endoscope in a digestive tract, the tangential direction of the permanent magnet rotating away from a lower gastric wall is opposite to the movement direction of the permanent magnet when the capsule endoscope is at the lower gastric wall of the digestive tract, and the tangential direction of the permanent magnet rotating away from a upper gastric wall is consistent with the movement direction of the permanent magnet when the capsule endoscope is at the upper gastric wall of the digestive tract.

19. The control system of claim 1, wherein the rotation and movement speed of the permanent magnet follows $v=\omega*L$, wherein v is the average movement speed of the permanent magnet, $\omega$ is the average rotation angular speed of the permanent magnet, and L is the length of the capsule endoscope.

20. The control system of claim 1, wherein the balance arm device is a spring assisted balance arm, comprising a base for providing support and a horizontal swing arm connected to the top of the base, wherein the other end of the horizontal swing arm connects with an upper balance arm, a lower balance arm, and a spring that are angled with the horizontal swing arm, the upper balance arm and the lower balance arm are parallel to each other, and the spring provides impetus for the upper balance arm and the lower balance arm to move upward or downward through deformation.

21. The control system of claim 20, wherein the spring is a common spring, a coil spring or a gas spring.

22. The control system of claim 20, wherein the horizontal swing arm is pivotally connected to the base, and is also pivotally connected to the upper balance arm and the lower balance arm, wherein the horizontal swing arm rotate 360 degrees horizontally along a pivot.

23. The control system of claim 20, wherein the boom is vertically connected to the other end of the upper balance arm, the lower balance arm and the spring.

24. The control system of claim 20, wherein the upper balance arm, the lower balance arm, and the horizontal swing arm are rigid arms.

25. The control system of claim 1, wherein the balance arm device is a pneumatic balance arm or a spring assisted balance arm.

26. The control system of claim 25, wherein the balance arm device and the mechanical arm are fixed to different fixing objects or a same fixing object.

27. The control system of claim 26, wherein the pneumatic balance arm is fixed to a column, and the spring assisted balance arm and the mechanical arm are fixed to a column, a base mounted on a wall surface or a base mounted on a ceiling.

* * * * *